United States Patent [19]

Pütter et al.

[11] 4,091,013
[45] May 23, 1978

[54] PROCESS FOR PREPARING 1-AMINO-NAPHTHALENE-7-SULPHONIC ACID

[75] Inventors: Rolf Putter, Dusseldorf; Günther Klag, Leverkusen; Heinz Ulrich Blank, Odenthal-Gloebusch, all of Germany

[73] Assignee: Bayer Aktiengesellschaft, Leverkusen, Germany

[21] Appl. No.: 706,099

[22] Filed: Jul. 16, 1976

[30] Foreign Application Priority Data

Aug. 7, 1975 Germany .............................. 2535337

[51] Int. Cl.² ..................... C07C 143/60; C07C 85/04
[52] U.S. Cl. ..................................... 260/508; 260/581
[58] Field of Search ................ 260/508, 510, 580, 581

[56] References Cited

U.S. PATENT DOCUMENTS

| 2,040,396 | 5/1936 | Morrell et al. | 260/508 |
| 2,266,228 | 12/1941 | Matthaeus et al. | 260/508 |
| 2,490,813 | 12/1949 | Hughes et al. | 260/581 |
| 3,231,616 | 1/1966 | Jones | 260/581 |
| 3,865,876 | 2/1975 | Chenevey et al. | 260/581 |

*Primary Examiner*—James O. Thomas, Jr.
*Assistant Examiner*—Werren B. Lone
*Attorney, Agent, or Firm*—Burgess, Dinklage & Sprung

[57] ABSTRACT

1-Amino-naphthalene-7-sulphonic acid is prepared by reacting 1-chloro-naphthalene-4,7-disulphonic acid with ammonia at elevated temperatures in the presence of water and optionally in the presence of a catalyst such as a copper catalyst.

8 Claims, No Drawings

PROCESS FOR PREPARING 1-AMINO-NAPHTHALENE-7-SULPHONIC ACID

BACKGROUND

This invention relates to a process for the preparation of 1-amino-naphthalene-7-sulphonic acid from 1-chloronaphthalene-4,7-disulphonic acid.

It is known that 1-amino-naphthalene-7-sulphonic acid can be prepared, for example, by sulphonating naphthalene, nitrating the resulting 2-naphthalenesulphonic acid and subsequently reducing this with iron (Beilstein H XIV, 765 and Ullmann, volume 12, 625 (1960)). 1-Amino-naphthalene-6-sulphonic acid is always formed as a by-product in this preparation and must be separated off.

The preparation of 1-amino-naphthalene-sulphonic acids by reacting the 1-chloro- and 1-bromo-naphthalene-sulphonic acids with ammonia at temperatures of 200° to 210° C is known (German Pat. No. 72,336). However, a disadvantage of this process is that the reaction proceeds very slowly when a catalyst is not used. According to German Pat. No. 72,336, if a reaction takes place, the corresponding 1-amino-monosulphonic, -disulphonic and -trisulphonic acids are respectively formed from 1-halogenonaphthalene monosulphonic, -disulphonic and -trisulphonic acids.

SUMMARY

A process for the preparation of 1-aminonaphthalene-7-sulphonic acid has now been found in which 1-chloro-naphthalene-4,7-disulphonic acid is reacted with ammonia at elevated temperature in the presence of water, optionally in a solvent and optionally in the presence of a catalyst.

DESCRIPTION

The preparation of 1-chloro-naphthalene-4,7-disulphonic acid, such as is employed for the process according to the invention, is in itself known. It can be prepared, for example, by sulphonation of 1-chloro-naphthalene-4-sulphonic acid (German Pat. No. 74,744 and Beilstein XI, page 214).

The process according to the invention can be illustrated by the following equation:

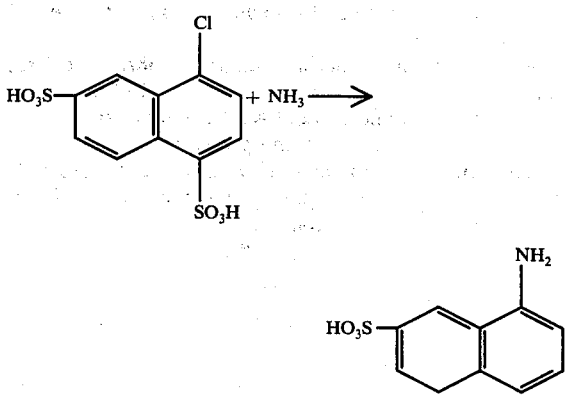

1-Chloronaphthalene-4,7-disulphonic acid can be employed in the process as the free acid or in the form of its acid or neutral salts and optionally also in an impure form. Preferred salts are, above all, the ammonium, alkali metal and alkaline earth metal salts, preferably the ammonium, sodium, potassium, magnesium and calcium salts. Possible impurities are, in addition to water and sulphuric acid, also chloronaphthalene-monosulphonic, -disulphonic and -trisulphonic acids as well as inorganic salts, such as, for example, NaCl and $Na_2SO_4$.

In general, according to the process of the invention, 1-chloro-naphthalene-4,7-disulphonic acid is reacted with an excess of ammonia. For example, 1 to 100 mols, preferably 2 to 50 mols, particularly preferentially 5 to 30 mols, of ammonia are employed per mol of 1-chloro-naphthalene-4,7-disulphonic acid.

A temperature range of 220° to 350° C, preferably 230° to 300° C, particularly preferentially 250° to 290° C may be mentioned as a preferred temperature range for the preparation of 1-aminonaphthalene-7-sulphonic acid. It is also possible first to prepare 1-aminonaphthalene-4,7-disulphonic acid from 1-chloronaphthalene-4,7-disulphonic acid at temperatures below 220° C, in a manner which is in itself known, and then, optionally after intermediate isolation of 1-aminonaphthalene-4,7-disulphonic acid, to raise the temperature, in the presence of ammonia and water, to 220° to 350° C and thus to obtain 1-aminonaphthalene-7-sulphonic acid.

The pressure is not critical for the process according to the invention; in general, the process is carried out under excess pressure, preferably under 20 to 250 bars, especially at 30 to 150 bars.

A catalyst is not essential in order to carry out the process according to the invention. In a preferred embodiment of the process according to the invention, 1-amino-naphthalene-7-sulphonic acid is prepared in the presence of a catalyst, for example a copper catalyst. Examples of copper catalysts which may be mentioned are copper and copper-I salts and copper-II salts, such as copper-I chloride, copper-II sulphate and copper-II acetate. Copper-I chloride may be mentioned as a preferred copper catalyst.

The process according to the invention can, for example, be carried out as follows:

1-Chloro-naphthalene-4,7-disulphonic acid in water, optionally with the addition of the copper catalyst, is initially introduced into an autoclave. Ammonia is then passed into the autoclave and the reaction is carried out at the requisite reaction temperature and under the pressure which arises during the reaction.

Working up of the reaction mixtures and the isolation of 1-amino-naphthalene-7-sulphonic acid are carried out in a manner which is in itself known. For example, the ammonia is separated off by distillation and the ammonium salt is obtained after distilling off ammonia and water. The corresponding alkali metal and alkaline earth metal salts of 1-amino-naphthalene-7-sulphonic acid are obtained by adding alkali metal salts and alkaline earth metal salts respectively, such as potassium chloride or calcium chloride. If necessary, these salts can be purified by recrystallisation. Free 1-amino-naphthalene-7-sulphonic acid is obtained by acidifying with mineral acids.

The ammonia which has not reacted during the reaction can be re-employed in a new conversion.

Surprisingly, in the process according to the invention, 1-amino-naphthalene-7-sulphonic acid, and not 1-aminonaphthalene-4,7-disulphonic acid, is formed in high yields and virtually without contamination by isomeric aminonaphthalene-sulphonic acids, which can be separated off only with difficulty.

1-Amino-naphthalene-7-sulphonic acid is a valuable intermediate product for the preparation of azo dyestuffs.

EXAMPLE 1

244 g (0.5 mol) of technical grade 66% strength 1-chloronaphthalenedisulphonic acid (Na salt) of the following composition: 66.3% of 1-chloronaphthalene-4,7-disulphonic acid, 11.2% of Na, 19% of water and 25.9% of C, with NaCl, $Na_2SO_4$ and $H_2SO_4$ as inorganic impurities, are dissolved in 750 ml of 25% strength ammonia and the solution is heated to 250° C for 7 hours in a V4A autoclave. The mixture is diluted with water to 1 liter, clarified with 2.5 g of active charcoal and filtered and the filtrate is concentrated to dryness. The residue is taken up in 200 ml of boiling 6 n hydrochloric acid.

The mixture is cooled to 10° C and filtered. The residue is dried in vacuo at 50° C and then ground.

104 g of a powder which consists to the extent of 80% of 1-aminonaphthalene-7-sulphonic acid is obtained; this corresponds to a yield of 75% of theory, based on the 1-chloronaphthalane-disulphonic acid employed. The reaction product contains: <0.1% of 1-aminonaphthalene-4,7-disulphonic acid, <0.1% of 1-chloronaphthalene-4,7-disulphonic acid and <0.1% of isomeric aminonaphthalene-monosulphonic acids.

EXAMPLE 2

100 g (0.2 mol) of technical grade 66% strength 1-chloronaphthalene-4,7-disulphonic acid (Na salt) of the following composition: 66.3% of 1-chloronaphthalene-4,7-disulphonic acid, 11.2% of Na, 19% of water and 25.9% of C, with NaCl, $Na_2SO_4$ and $H_2SO_4$ as inorganic impurities, are dissolved in 200 ml of 25% strength ammonia and 100 ml of water and the solution is heated, with the addition of 1 g of Cu(I)Cl, to 280° C for 8 hours in an autoclave. After cooling to room temperature, the batch is concentrated to dryness. The residue is dissolved in 350 ml of water and the solution is clarified with 2 g of active charcoal and filtered. The filtrate is acidified to pH 2 with concentrated hydrochloric acid. It is cooled to 10° C and filtered. The crystalline material on the filter is dried at 50° C/200 mm Hg. 40.6 g of a powder which consists to the extent of 78% of 1-aminonaphthalene-7-sulphonic acid are obtained; this corresponds to a yield of 71% of theory, based on the 1-chloronaphthalene-disulphonic acid employed. The reaction product contains: <0.1% of 1-aminonaphthalene-4,7-disulphonic acid, <0.1% of 1-chloronaphthalene-4,7-disulphonic acid and <0.1% of isomeric aminonaphthalene-monosulphonic acids.

EXAMPLE 3

100 g (0.2 mol) of technical grade 66% strength 1-chloronaphthalene-4,7-disulphonic acid (Na salt) of the following composition: 66.3% of 1-chloronaphthalene-4,7-disulphonic acid, 11.2% of Na, 19% of water and 25.9% of C, with NaCl, $Na_2SO_4$ and $H_2SO_4$ as inorganic impurities, are dissolved in 300 ml of 25% strength ammonia and the solution is heated, with the addition of 1 g of Cu(I)Cl, to 270° C for 4 hours in a V4A autoclave. After cooling to room temperature, the batch is concentrated to dryness and the residue is dried at 50°/200 mm Hg.

91.2 g of a crude product which consists to the extent of 39.1% of 1-aminonaphthalene-7-sulphonic acid are obtained; this corresponds to a yield of 78% of theory, based on the 1-chloronaphthalene-disulphonic acid employed. The crude product contains: about 1% of 1-aminonaphthalene-4,7-disulphonic acid, about 2% of 1-chloronaphthalene-4,7-disulphonic acid and <0.7% of isomeric aminonaphthalene-monosulphonic acids.

What is claimed is:

1. Process for preparing 1-amino-naphthalene-7-sulphonic acid which comprises reacting 1-chloro-naphthalene-4,7-disulphonic acid with ammonia at temperatures of 220° to 350° C in the presence of water.

2. Process of claim 1 wherein 1 to 100 mols of ammonia are employed per mol of 1-chloro-naphthalene-4,7-disulphonic acid.

3. Process of claim 2 wherein 2 to 50 mols of ammonia are employed.

4. Process of claim 1 wherein the temperature is 230° to 300° C.

5. Process of claim 1 wherein 1-aminonaphthalene-4,7-disulphonic acid is prepared from 1-chloronaphthalene-4,7-disulphonic acid at temperatures below 220° C, and then the temperature of the reaction mixture is raised to 220° to 350° C in the presence of ammonia and water so as to obtain 1-aminonaphthalene-7-sulphonic acid.

6. Process of claim 1 wherein 1-chloronaphthalene-4,7-disulphonic acid is in the form of its acid or its acid or neutral salts, or in an inpure form.

7. Process of claim 1 wherein 1-aminoaphthalene-4,7-disulphonic acid is prepared from 1-chloronaphthalene-4,-7-disulphonic acid at temperatures below 220° C, and then after intermediate isolation of 1-aminonaphthalene-4,7-disulphonic acid, the temperature of the reaction mixture is raised to 220° to 350° in the presence of ammonia and water so as to obtain 1-aminoaphthalene-7-sulphonic acid.

8. Process for preparing 1-amino-naphthalene-7-sulphonic acid which comprises reacting 1-chloro-naphthalene-4,7-disulphonic acid with ammonia at temperatures of 220° to 350° C in the presence of water and in the presence of a copper salt catalyst selected from the group consisting of copper-I-chloride, copper-II-sulphate and copper-II-acetate.

* * * * *